US012622704B2

(12) United States Patent
Ogawa et al.

(10) Patent No.: US 12,622,704 B2
(45) Date of Patent: May 12, 2026

(54) MEDICAL DEVICE WITH TUBE AND BASKET

(71) Applicant: KANEKA CORPORATION, Osaka (JP)

(72) Inventors: Atsushi Ogawa, Tokyo (JP); Masayuki Takatera, Settsu (JP)

(73) Assignee: KANEKA CORPORATION, Osaka (JP)

( * ) Notice: Subject to any disclaimer, the term of this patent is extended or adjusted under 35 U.S.C. 154(b) by 44 days.

(21) Appl. No.: 18/827,373

(22) Filed: Sep. 6, 2024

(65) Prior Publication Data

US 2024/0423633 A1    Dec. 26, 2024

Related U.S. Application Data

(63) Continuation of application No. PCT/JP2023/006366, filed on Feb. 22, 2023.

(30) Foreign Application Priority Data

Mar. 8, 2022    (JP) ................................. 2022-034902

(51) Int. Cl.
*A61B 17/12* (2006.01)
*A61B 17/00* (2006.01)

(52) U.S. Cl.
CPC .. *A61B 17/12145* (2013.01); *A61B 17/12113* (2013.01); *A61B 2017/00862* (2013.01); *A61B 2017/1205* (2013.01)

(58) Field of Classification Search
CPC ........ A61B 17/12145; A61B 17/12113; A61B 2017/00862; A61B 2017/1205
See application file for complete search history.

(56) References Cited

U.S. PATENT DOCUMENTS

| | | | |
|---|---|---|---|
| 5,733,294 A | 3/1998 | Forber et al. | |
| 2007/0078481 A1 | 4/2007 | Magnuson et al. | |

(Continued)

FOREIGN PATENT DOCUMENTS

| | | | |
|---|---|---|---|
| DE | 20 2009 001 951 U1 | 4/2010 | |
| EP | 2 301 449 A2 | 3/2011 | |

(Continued)

OTHER PUBLICATIONS

International Search Report for PCT/JP2023/006365 (PCT/ISA/210) mailed on Apr. 11, 2023.

(Continued)

*Primary Examiner* — Phong Son H Dang
(74) *Attorney, Agent, or Firm* — Birch, Stewart, Kolasch & Birch, LLP

(57) ABSTRACT

A medical device comprising: an outer tube, a basket, and a basket pusher, wherein the basket includes a first bundling portion at which the plurality of wires are fixed at a distal portion of the basket, and a second bundling portion at which the plurality of wires are fixed at a proximal portion of the basket, in a state where the basket is accommodated in the outer tube, the first bundling portion has a first end being an end portion on a far side with respect to the second bundling portion and a second end being an end portion on a near side with respect to the second bundling portion, and as the basket comes out of the outer tube, an angle on the proximal side between an extending direction of the outer tube and a straight line passing through the first end and the second end becomes smaller.

13 Claims, 4 Drawing Sheets

(56)  References Cited

U.S. PATENT DOCUMENTS

| 2009/0062841 A1* | 3/2009 | Amplatz .......... A61B 17/12159 |
| | | 606/200 |
| 2009/0227976 A1 | 9/2009 | Calabria et al. |
| 2009/0275974 A1* | 11/2009 | Marchand ........ A61B 17/12145 |
| | | 87/8 |
| 2013/0060276 A1 | 3/2013 | Hocking |
| 2013/0245667 A1 | 9/2013 | Marchand et al. |
| 2015/0105817 A1 | 4/2015 | Marchand et al. |
| 2015/0150563 A1 | 6/2015 | Marchand et al. |
| 2015/0272589 A1 | 10/2015 | Lorenzo |
| 2016/0089170 A1 | 3/2016 | Davis et al. |
| 2016/0249935 A1* | 9/2016 | Hewitt .............. A61B 17/1215 |
| | | 606/200 |
| 2017/0215911 A1 | 8/2017 | Nakajima et al. |
| 2018/0000489 A1 | 1/2018 | Marchand et al. |
| 2018/0242978 A1 | 8/2018 | Chou et al. |
| 2018/0242979 A1 | 8/2018 | Lorenzo |
| 2018/0280042 A1 | 10/2018 | Okada |
| 2018/0317945 A1 | 11/2018 | Okada et al. |
| 2019/0008522 A1 | 1/2019 | Lorenzo |
| 2019/0374232 A1 | 12/2019 | Lorenzo |
| 2020/0281603 A1 | 9/2020 | Marchand et al. |
| 2020/0375606 A1 | 12/2020 | Lorenzo |
| 2021/0007755 A1 | 1/2021 | Lorenzo et al. |
| 2021/0177429 A1 | 6/2021 | Lorenzo |
| 2021/0282789 A1 | 9/2021 | Vu et al. |
| 2021/0330331 A1 | 10/2021 | Lorenzo |

FOREIGN PATENT DOCUMENTS

| JP | 1-95910 U | 6/1989 |
| JP | 2002-253559 A | 9/2002 |
| JP | 2009-509719 A | 3/2009 |
| JP | 2011-519632 A | 7/2011 |
| JP | 2011-244927 A | 12/2011 |
| JP | 2013-5859 A | 1/2013 |
| JP | 2015-196092 A | 11/2015 |
| JP | 2017-136188 A | 8/2017 |
| JP | 2020-508173 A | 3/2020 |
| WO | WO2017/141374 A1 | 8/2017 |
| WO | WO2017/203669 A1 | 11/2017 |

OTHER PUBLICATIONS

International Search Report for PCT/JP2023/006366 (PCT/ISA/210) mailed on Apr. 4, 2023.

Written Opinion of the International Searching Authority for PCT/JP2023/006365 (PCT/ISA/237) mailed on Apr. 11, 2023.

Written Opinion of the International Searching Authority for PCT/JP2023/006366 (PCT/ISA/237) mailed on Apr. 4, 2023.

* cited by examiner

[Fig. 1]
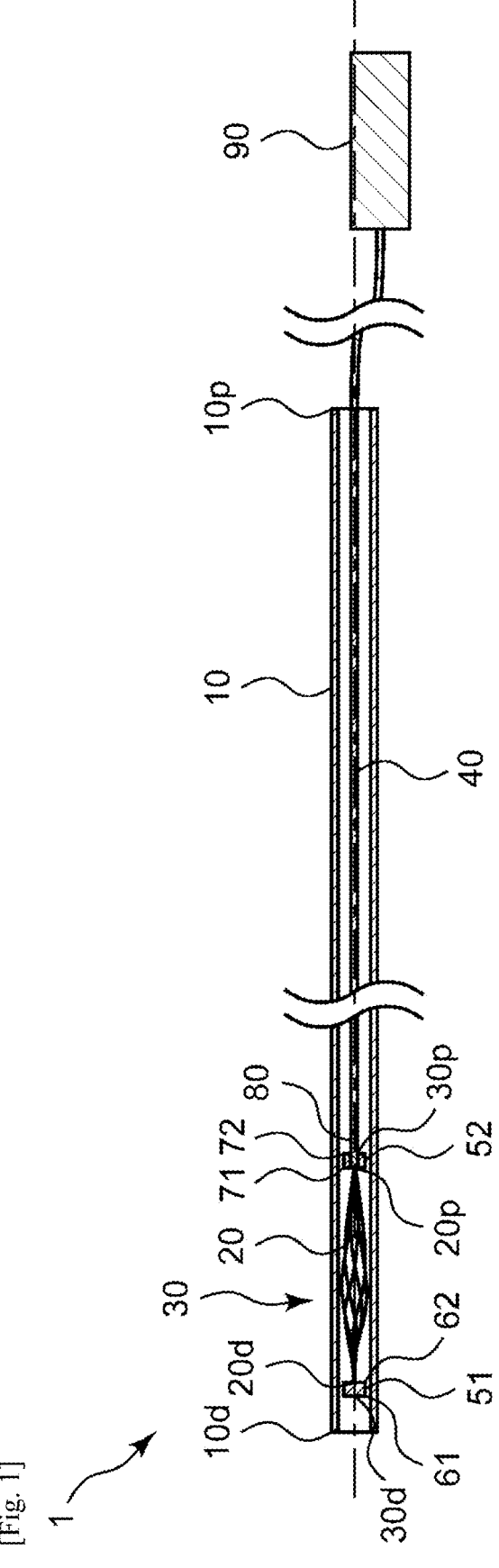

[Fig. 2]
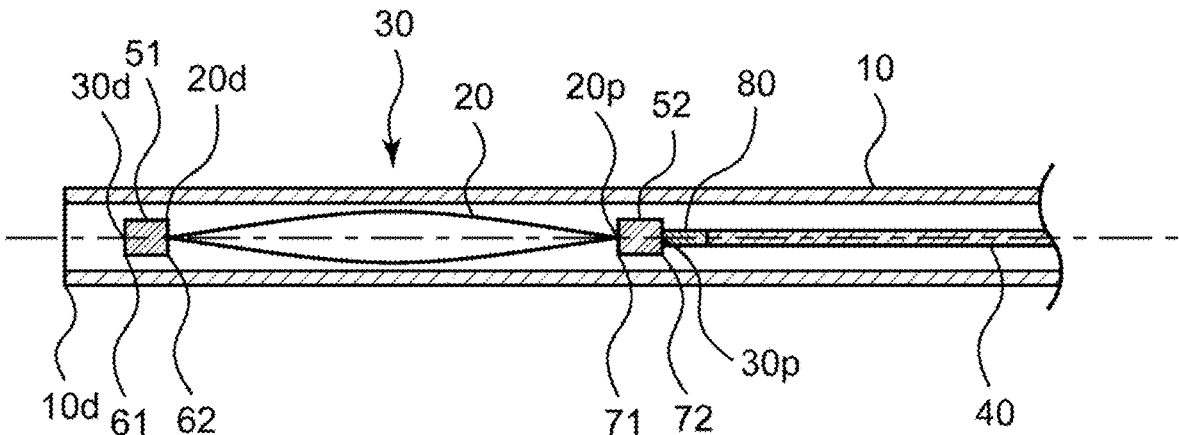
[Fig. 3]
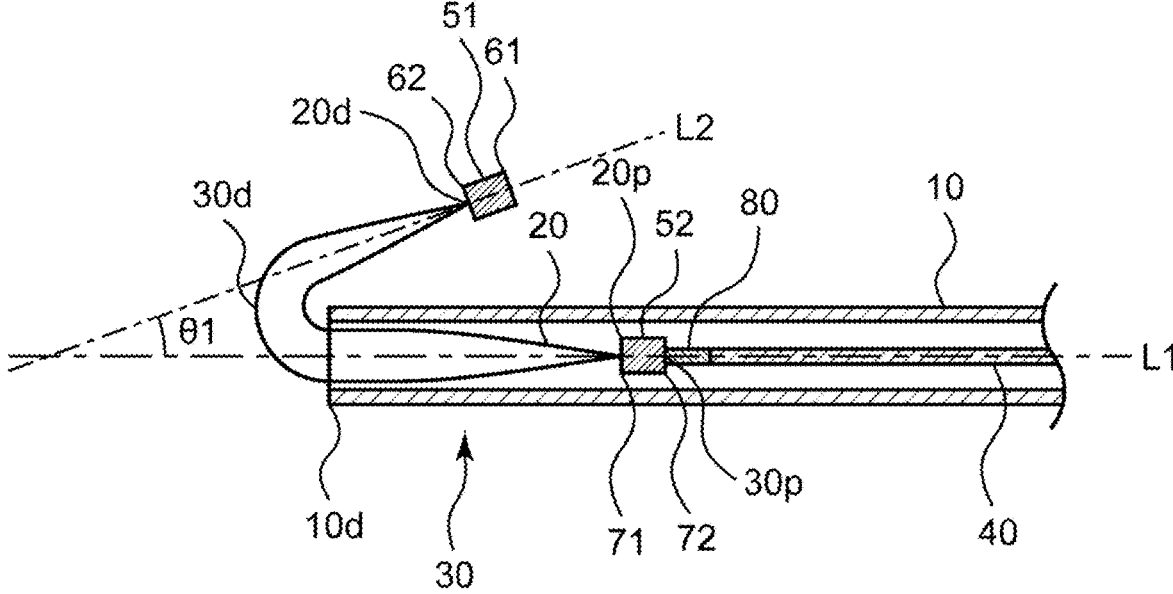

[Fig. 4]
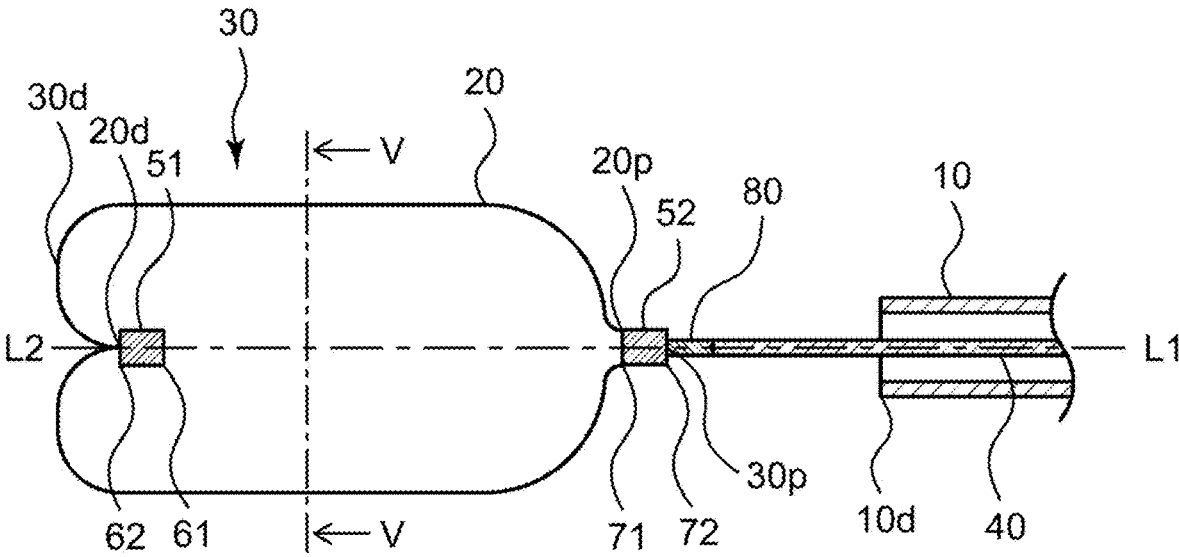
[Fig. 5]
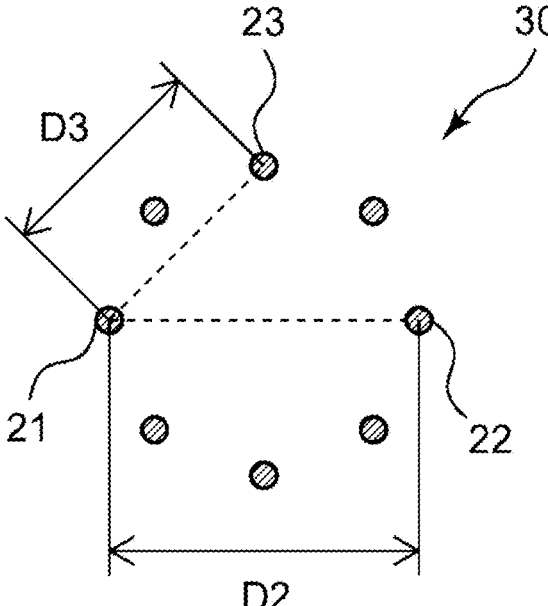

[Fig. 6]
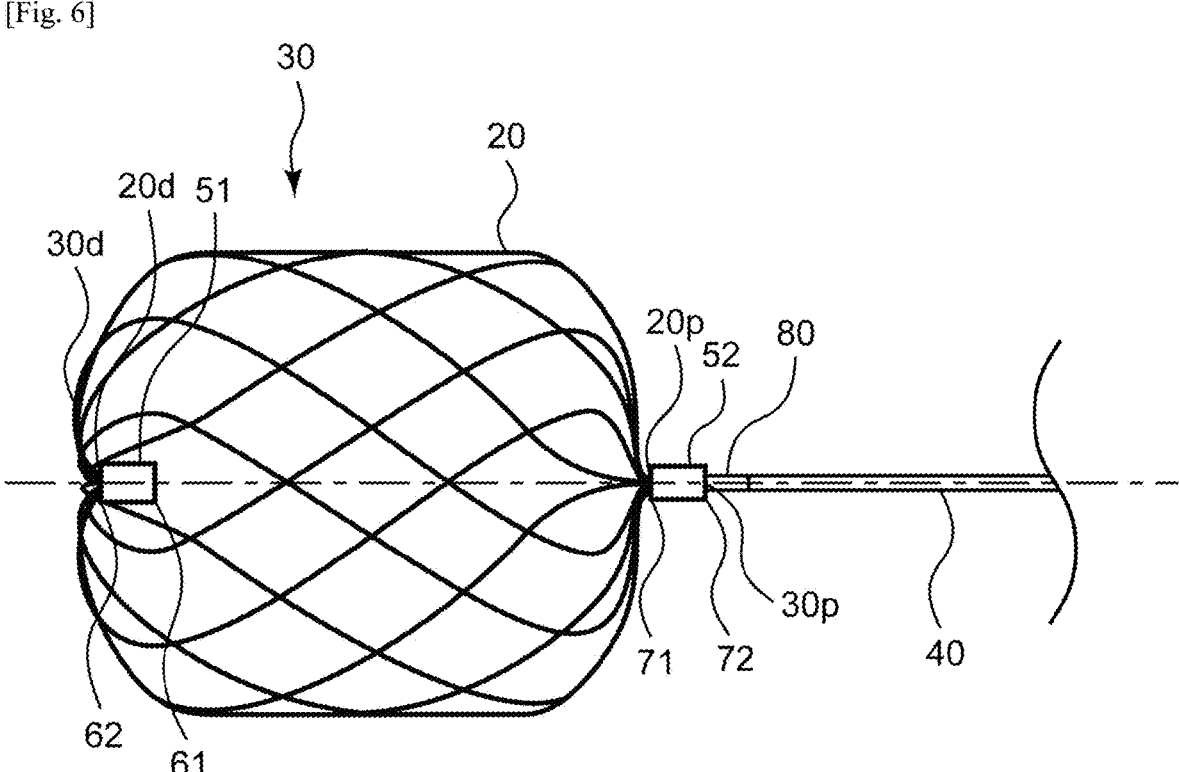

MEDICAL DEVICE WITH TUBE AND BASKET

CROSS REFERENCE TO RELATED APPLICATIONS

This application is a Continuation of PCT International Application No. PCT/JP2023/006366, filed on Feb. 22, 2023, which claims priority under 35 U.S.C. 119 (a) to Patent Application No. 2022-034902, filed in Japan on Mar. 8, 2022, all of which are hereby expressly incorporated by reference into the present application.

TECHNICAL FIELD

The present invention relates to a medical device that is used for a blood vessel or an in-vivo lumen of a digestive organ or the like.

BACKGROUND ART

In treatment of an in-vivo lumen, a device having a basket is used in some cases. Specific examples include: a treatment in which an abnormal object such as a thrombus generated in a blood vessel or a calculus generated in a digestive organ tract such as a bile duct is trapped inside a basket and removed; and embolization in which a basket is indwelled in a vascular lesion portion such as an aneurysm to alter the blood flow to prevent rupture of the bulge. Further, embolization in which a basket is disposed in a bulge and a coil is packed in this basket to fill the bulge, thereby preventing rupture of the bulge, is also known.

For example, Patent Literature 1 describes an embolic protection device for use in a lumen. The embolic protection device includes: a core wire; and a cannula attached to the core wire and extending in the proximal direction about the core wire. The cannula forms a basket portion including a plurality of struts and a filter portion. The filter portion has a plurality of openings formed in the cannula. The basket portion is movable between an expanded state and a collapsed state. Patent Literature 2 describes a catheter device that has: a catheter to be inserted into a lumen of a human body; a branch portion connected to a base end portion of the catheter and provided with an insertion hole for allowing passage therethrough of a guide wire to be used when the catheter is inserted into a lumen of the human body; and a liquid introducing means that introduces a liquid such as a drug solution into the catheter through a tube connected to the branch portion. At the leading end of the catheter, an embolus trapping means for trapping an embolus in a lumen of the human body is disposed. The embolus trapping means is formed by a net member that opens and closes in a parachute shape with the interval between both ends thereof being reduced or increased. Patent Literature 3 describes a device that includes a self-expandable-type resilient permeable shell. The self-expandable-type resilient permeable shell includes a plurality of elongated resilient filaments with a woven structure fixed to each other at proximal ends and distal ends of the filaments. Further, the self-expandable-type resilient permeable shell has: a radially constrained elongated state configured for delivery within a microcatheter, with the thin woven filaments extending longitudinally from the proximal end to the distal end radially adjacent to each other along the lengths of the filaments; and an expanded relaxed state with a globular longitudinally shortened configuration relative to the radially constrained state, with the woven filaments forming the self-expandable-type resilient permeable shell in a smooth path radially expanded from the longitudinal axis between the proximal end and the distal end including a plurality of openings in the shell formed between the woven filaments. The largest of the openings is configured to allow blood flow through the openings at a velocity below a thrombotic threshold velocity. Patent Literature 4 describes an embolus trapping device that includes: a long shaft member whose leading end side is sent into a lumen; a leading end guide portion that is flexible and disposed at the leading end of the shaft member; and an embolus trapping filter having a filter portion provided on the base end side of the leading end guide portion and composed of a mesh formed by wires having elasticity or shape memory properties, the filter portion having a basket shape that contracts in a catheter for device transport and expands when released from the catheter into a lumen, and a bundling portion at which the wires forming the filter portion are bundled at each of the leading end side and the base end side. The embolus trapping device is disposed such that the opening of the filter portion is oriented toward the leading end side of the shaft member and opposed to the blood flow, thereby trapping an embolus released in the lumen. Patent Literature 5 describes an occlusion device including: a substantially tubular structure that has a proximal end region and a distal end region, that has a first expanded state and a second collapsed state, that has, in the second collapsed state, dimensions suitable for insertion through the vascular system of a patient into the neck of an aneurysm, that has an outer surface capable of coming into contact with the aneurysm in the expanded state, and that further has an inner surface; and a control ring disposed in the proximal end region of the structure and having a substantially annular body at least substantially surrounding the proximal end region in order to prevent expansion in the radial direction of the proximal end region and to provide an engagement feature during operation of the occlusion device. Patent Literature 6 describes a system including: a braided tubular implant having a distal implant end portion and a proximal implant end portion, and being invertible about the distal implant end portion; and a tubular delivery member around the braided tubular implant, the tubular delivery member having a distal end portion releasably connected to the distal implant end portion, wherein translation of the braided tubular implant distally from the tubular member causes the braided tubular implant to be inverted and collapsed into itself, thereby forming an occlusive sack configured to occlude an aneurysm.

CITATION LIST

Patent Literature

PATENT LITERATURE 1: JP 2009-509719 T
PATENT LITERATURE 2: JP 2011-244927 A
PATENT LITERATURE 3: JP 2011-519632 T
PATENT LITERATURE 4: JP 2013-5859 A
PATENT LITERATURE 5: JP 2015-196092 A
PATENT LITERATURE 6: JP 2020-508173 T

SUMMARY OF INVENTION

Technical Problem

In the devices as in Patent Literatures 1 to 5, a bundling portion at which wires forming a basket are bundled is present at a distal end portion of the basket. Thus, there has been a problem that this bundling portion may come into contact with the tube wall of an in-vivo lumen, thereby damaging the tube wall.

In the system as in Patent Literature 6, the distal end portion of the braided tubular implant is invertible about the longitudinal axis and is collapsed inside the braided tubular implant. Therefore, there has been a problem that the configuration of such a system becomes complicated, and the diameter of the microcatheter in which the braided tubular implant is disposed during delivery becomes large. Thus, there has been room for improvement in order to realize further minimal invasiveness. The system as in Patent Literature 6 also has a problem that, since the diameter of the microcatheter is large, it is difficult to perform treatment of a peripheral artery.

The present invention has been made in view of the circumstances described above. An object of the present invention is to provide a medical device that is less likely to damage, in an in-vivo lumen, a tube wall or the like of a living body, that is minimally invasive, and with which treatment of a peripheral artery is easily performed.

Solution to Problem

A medical device that has solved the above problems is as follows.

[1] A medical device comprising:

an outer tube having a distal end and a proximal end;

a basket disposed in an inner cavity of the outer tube and having a plurality of wires, the basket being expandable when having come out of the outer tube; and a basket pusher disposed on a proximal side with respect to the basket, wherein the basket includes a first bundling portion at which the plurality of wires are bundled and fixed at a distal portion of the basket, and a second bundling portion at which the plurality of wires are bundled and fixed at a proximal portion of the basket, in a state where the basket is accommodated in the outer tube, the first bundling portion has a first end being an end portion on a far side with respect to the second bundling portion and a second end being an end portion on a near side with respect to the second bundling portion, and in at least a partial section of the basket, as the basket comes out of the outer tube, an angle on the proximal side between an extending direction of a leading end portion of the outer tube and a straight line passing through the first end and the second end becomes smaller.

[2] The medical device according to [1], wherein in a state where a predetermined length of the basket has come out of the outer tube, the second end is positioned on a distal side with respect to the first end.

[3] The medical device according to [1] or [2], wherein when a predetermined length of the basket has come out of the outer tube, the angle on the proximal side between the extending direction of the leading end portion of the outer tube and the straight line passing through the first end and the second end becomes 0 degrees or more and 90 degrees or less (including 0 degrees), and the predetermined length is a length of $1/10$ or more and $3/4$ or less of a length from a proximal end of the basket to a distal end of the basket.

[4] The medical device according to any one of [1] to [3], wherein in a state where an entirety of the basket has come out of the outer tube and no external force is applied to the basket, the angle on the proximal side between the extending direction of the outer tube and the straight line passing through the first end and the second end of the first bundling portion is more than 90 degrees and 180 degrees or less (including 180 degrees).

[5] The medical device according to any one of [1] to [4], wherein in a state where an entirety of the basket has come out of the outer tube and no external force is applied to the basket, the second end is positioned on a distal side with respect to the first end.

[6] The medical device according to [1], wherein in a state where a predetermined length of the basket has come out of the outer tube, the first bundling portion is positioned outside the basket, and in a state where an entirety of the basket has come out of the outer tube and no external force is applied to the basket, the first bundling portion is positioned inside the basket.

[7] The medical device according to any one of [1] to [6], wherein the plurality of wires of the basket include a first wire group and a second wire group, and a length of the wire of the first wire group is shorter than a length of the wire of the second wire group.

[8] The medical device according to [7], wherein the plurality of wires of the basket further include a third wire group, a length of the wire of the third wire group is longer than the length of the wire of the first wire group and shorter than the length of the wire of the second wire group, and in a cross-section perpendicular to an extending direction of the basket pusher, a distance between the first wire group and the second wire group is longer than a distance between the first wire group and the third wire group.

[9] The medical device according to any one of [1] to [8], wherein in the state where the basket is accommodated in the outer tube, the second bundling portion has one end being an end portion on a near side with respect to the first bundling portion and another end being an end portion on a far side with respect to the first bundling portion, and in a state where an entirety of the basket has come out of the outer tube and no external force is applied to the basket, the one end is positioned on a distal side with respect to the other end.

[10] The medical device according to any one of [1] to [9], comprising a connection member on the proximal side with respect to the basket and on a distal side with respect to the basket pusher.

[11] The medical device according to any one of [1] to [10], wherein the first bundling portion and the second bundling portion include a radiopaque material.

[12] The medical device according to any one of [1] to [11], wherein each wire of the basket includes a superelastic alloy.

[13] The medical device according to any one of [1] to [12], wherein each wire of the basket includes a radiopaque material.

Advantageous Effects of Invention

According to the medical device of the present invention, in the state where the basket is accommodated in the outer tube, the first bundling portion has the first end being an end portion on the far side with respect to the second bundling portion and the second end being an end portion on the near side with respect to the second bundling portion, and in at least a partial section of the basket, as the basket comes out of the outer tube, the angle on the proximal side between the extending direction of the leading end portion of the outer tube and the straight line passing through the first end and the second end becomes smaller. Accordingly, in a process where the basket accommodated in the outer tube comes out of the outer tube, the distal end portion of the basket enters a state of being bent. Therefore, when the basket is released from the outer tube, the first bundling portion of the basket is less likely to come into contact with the tube wall of the in-vivo lumen, and thus, can be less likely to damage the tube wall. Accordingly, a medical device that is minimally invasive can be realized.

BRIEF DESCRIPTION OF DRAWINGS

FIG. 1 shows a cross-sectional view, parallel to the longitudinal direction of an outer tube, of a medical device according to an embodiment of the present invention.

FIG. 2 shows a cross-sectional view, parallel to the longitudinal direction of the outer tube, of a distal end portion of the medical device shown in FIG. 1 in a state where a basket is accommodated in the outer tube.

FIG. 3 shows a cross-sectional view, parallel to the longitudinal direction of the outer tube, of the distal end portion of the medical device shown in FIG. 1 in a state where a predetermined length of the basket has come out of the outer tube.

FIG. 4 shows a cross-sectional view, parallel to the longitudinal direction of the outer tube, of the distal end portion of the medical device shown in FIG. 1 in a state where the entirety of the basket has come out of the outer tube and no external force is applied to the basket.

FIG. 5 shows a V-V cross-sectional view of the basket of the medical device shown in FIG. 4.

FIG. 6 shows an example of the basket of a medical device according to an embodiment of the present invention.

DESCRIPTION OF EMBODIMENTS

Hereinafter, the present invention is specifically described below based on the following embodiments; however, the present invention is not restricted by the embodiments described below of course, and can be certainly put into practice after appropriate modifications within in a range meeting the gist of the above and the below, all of which are included in the technical scope of the present invention. In the drawings, hatching or a reference sign for a member may be omitted for convenience, and in such a case, the description and other drawings should be referred to. In addition, sizes of various members in the drawings may differ from the actual sizes thereof, since priority is given to understanding the features of the present invention.

FIG. 1 is a cross-sectional view, parallel to the longitudinal direction, of an outer tube 10 in a medical device 1 according to an embodiment of the present invention. FIG. 2 is a cross-sectional view, parallel to the longitudinal direction of the outer tube 10, of a distal end portion of the medical device 1 in a state where a basket 30 is accommodated in the outer tube 10. FIG. 3 is a cross-sectional view, parallel to the longitudinal direction of the outer tube 10, of the distal end portion of the medical device 1 in a state where a predetermined length of the basket 30 has come out of the outer tube 10. FIG. 6 is a diagram of an example of the basket 30. In FIG. 2 and FIG. 3, for easy understanding of the positional relationship between a first bundling portion 51, a second bundling portion 52, a first end 61, and a second end 62, only some of a plurality of wires 20 of the basket 30 are shown, and the other wires are not shown.

As shown in FIG. 1 to FIG. 3, the medical device 1 of the present invention has: the outer tube 10 having a distal end 10d and a proximal end 10p; the basket 30 disposed in an inner cavity of the outer tube 10 and having a plurality of wires 20, the basket being expandable when having come out of the outer tube 10; and a basket pusher 40 disposed on the proximal side with respect to the basket 30. The basket 30 includes the first bundling portion 51 at which the plurality of wires 20 are bundled and fixed at a distal portion of the basket 30, and the second bundling portion 52 at which the plurality of wires 20 are bundled and fixed at a proximal portion of the basket 30. In a state where the basket 30 is accommodated in the outer tube 10, the first bundling portion 51 has the first end 61 being an end portion on the far side with respect to the second bundling portion 52 and the second end 62 being an end portion on the near side with respect to the second bundling portion 52. In at least a partial section of the basket 30, as the basket 30 comes out of the outer tube 10, an angle θ1 on the proximal side between an extending direction L1 of a leading end portion of the outer tube 10 and a straight line L2 passing through the first end 61 and the second end 62 becomes smaller.

The medical device 1 can be used in: a treatment in which an abnormal object present in an in-vivo lumen such as a thrombus generated in a blood vessel or a calculus generated in a digestive organ tract such as a bile duct is trapped inside the basket 30 and removed from the in-vivo lumen; embolization in which the basket 30 is indwelled in a vascular lesion portion such as an aneurysm to promote thrombosis to prevent rupture of the bulge; and the like. The medical device 1 introduces the outer tube 10 into an in-vivo lumen and causes the basket 30 to be indwelled in a target site from the outer tube 10. In embolization, for example, the basket 30 is disposed in a bulge in a terminal portion of an in-vivo lumen, a bulge in a side wall portion of an in-vivo lumen, a main tube peripheral portion of an in-vivo lumen, or the like. Then, a medical long object is indwelled inside the basket 30 disposed in the bulge, the main tube peripheral portion, or the like to promote thrombosis of the bulge. Examples of the medical long object include a coil, a wire, and a string-like object. Further, the medical long object may be a tube for transporting a long object such as a coil. In addition, the tubular medical long object may be for transporting a semi-solid fluid, a gel-like material, a semi-solid, a liquid, or the like, or further, a bag-like object, into a bulge. The liquid for the tubular medical long object may be a liquid that hardens or a liquid that is deposited, for example.

As shown in FIG. 1, the outer tube 10 has the distal end 10d and the proximal end 10p. In the present invention, the proximal side refers to the hand side of a user with respect to the extending direction of the outer tube 10, and the distal side refers to the side opposite to the proximal side, i.e., the side (lesion portion side) where a treatment is performed by the medical device 1. The extending direction of the outer tube 10 is referred to as a longitudinal direction. In other words, the longitudinal direction of the outer tube 10 is a distal-proximal direction of the outer tube 10. In FIG. 1 to FIG. 3, the right side of the drawing is the proximal side and the left side of the drawing is the distal side.

The outer tube 10 is a tubular member extending in the longitudinal direction and has at least one lumen extending in the longitudinal direction. The number of the lumens of the outer tube 10 may be plural, but is preferably one. When the number of the lumens of the outer tube 10 is one, the outer diameter of the outer tube 10 can be reduced. As a result, the minimal invasiveness of the medical device 1 can be improved.

The material forming the outer tube 10 is preferably a resin or a metal. Examples of the resin forming the outer tube 10 include polyamide-based resins, polyester-based resins, polyurethane-based resins, polyolefin-based resins, fluorine-based resins, vinyl chloride-based resins, silicone-based resins, natural rubber, etc. Only one of these materials may be used, or two or more of these materials may be used in combination. Among them, the resin forming the outer tube 10 is preferably at least one of polyamide-based resins, polyester-based resins, polyurethane-based resins, poly-olefin-based resins, and fluorine-based resins. When the material forming the outer tube 10 is at least one of poly-amide-based resins, polyester-based resins, polyurethane-based resins, polyolefin-based resins, and fluorine-based resins, the slipperiness of the surface of the outer tube 10 can be enhanced, and the insertability of the outer tube 10 into a lumen such as a blood vessel can be improved. A tube, to serve as the outer tube 10, that is formed from the resin can be produced by using a normal method such as extrusion molding and injection molding.

Examples of the metal forming the outer tube 10 include stainless steel such as SUS304 and SUS316, platinum, nickel, cobalt, chromium, titanium, tungsten, gold, Ni—Ti alloys, Co—Cr alloys, and combinations thereof. As a tube, to serve as the outer tube 10, that is formed from the metal, a tube obtained by spirally winding a metal wire material, a tube obtained by braiding metal wire materials, or the like may be used. In addition, the outer tube 10 may be a tube obtained by combining a metal and a resin. A tubular body formed from a resin and having a reinforcing material such as a metal wire material provided therein may be used as the outer tube 10. In the case where a tube-like member made of a resin and having a wire material provided therein is used as the outer tube 10, the wire material is preferably formed from a Ni—Ti alloy since the wire material has excellent shape memory properties and high elasticity. The wire material may be a fiber material of the above-described metal, a polyarylate fiber, an aramid fiber, an ultra-high molecular weight polyethylene fiber, a PBO fiber, a carbon fiber, or the like. The fiber material may be a monofilament or may be a multifilament.

The outer tube 10 may be composed of a single layer or may be composed of a plurality of layers. In addition, in the longitudinal direction, a part of the outer tube 10 may be composed of a single layer, and the other part of the outer tube 10 may be composed of a plurality of layers.

With respect to the outer tube 10, the outer surface of the outer tube 10 is preferably coated with a hydrophilic resin. That is, the outer tube 10 preferably has a hydrophilic resin layer outside the outer tube 10. When the outer surface of the outer tube 10 is coated with a hydrophilic resin, the slip-periness of the outer tube 10 can be enhanced, and insert-ability in an in-vivo lumen can be enhanced.

With respect to the outer tube 10, the inner surface of the outer tube 10 is preferably coated with a fluorine-based resin. In other words, the outer tube 10 preferably has a fluorine-based resin layer inside the outer tube 10. When the outer tube 10 has a fluorine-based resin layer inside the outer tube 10, the slipperiness of the inner surface the outer tube 10 is improved. Therefore, in the inner cavity of the outer tube 10, the basket 30 is easily moved in the longitudinal direction.

The cross-sectional shape of the outer shape of the outer tube 10 in a cross-section perpendicular to the longitudinal direction may be a circular shape, an elliptical shape, a polygonal shape, or a combination thereof. In addition, the cross-sectional shape of the inner cavity of the outer tube 10 in a cross-section perpendicular to the longitudinal direction may also be a circular shape, an elliptical shape, a polygonal shape, or a combination thereof.

As shown in FIG. 1 to FIG. 3, the basket 30 is disposed in the inner cavity of the outer tube 10, has the plurality of wires 20, and is expandable when having come out of the outer tube 10. That is, the basket 30 is disposed in the lumen of the outer tube 10, and when released from the outer tube 10, the basket 30 becomes able to expand. When disposed in the inner cavity of the outer tube 10, the basket 30 is in contact with the inner wall of the outer tube 10, and is in a state of being squeezed under an external force from the outer tube 10. When the basket 30 is released from the outer tube 10, the external force is not applied any more, and the basket 30 enters an expanded state if no other external force is applied. When the basket 30 is disposed in a bulge, the basket 30 comes into contact with the bulge wall, to be subjected to an external force from the bulge and deformed.

The material forming each wire 20 preferably has elas-ticity, and examples thereof include metal wire materials that are single wires, flat wires, multi-wires, composite material wires, or twisted wires formed from stainless steel such as SUS304 and SUS316, platinum, nickel, cobalt, chromium, titanium, tungsten, aluminum, gold, silver, Ni—Ti alloys, Co—Cr alloys, etc. Among them, the material forming each wire 20 is preferably a material having superelasticity, and more preferably a metal wire material of a Ni—Ti alloy. When the material forming each wire 20 is a metal wire material of a Ni—Ti alloy, the elasticity of each wire 20 can be enhanced, and even if the deformation amount of the basket 30 released from the outer tube 10 is large, the return amount is large, and thus, the basket 30 can be less likely to lose its shape.

It is sufficient that the number of the wires 20 of the basket 30 is plural, and the number of the wires 20 can be selected according to the inner diameter of an in-vivo lumen or the like. In the drawings, the number of the wires 20 of the basket 30 is limited. However, in the embodiment of the present invention, the basket 30 can be, for example, a basket 30 including 8 or more and 64 or less wires 20. The diameter of each element wire of each wire 20 can be set according to the size of the basket 30, the number and the material of the wires 20, and the like. The number of the wires 20 of the basket 30 is preferably 16 or more and 32 or less.

Preferably, the basket 30 is deformable and is slidable inside a tube having an inner diameter of 0.021 inches (0.5334 mm) or less, and more preferably slidable inside a tube having an inner diameter of 0.017 inches (0.4318 mm) or less. In the case where the number of the lumens of the outer tube 10 is one, preferably, the inner diameter of the outer tube 10 is 0.017 inches or less, and the basket 30 is disposed in the inner cavity of this outer tube 10. In the case where the outer tube 10 has a plurality of lumens, the inner diameter of the lumen in which the basket 30 is disposed is preferably 0.017 inches or less. When the basket 30 is deformable and is slidable inside a tube having an inner diameter of 0.017 inches or less, the outer diameter of the outer tube 10 can be reduced. Accordingly, the medical device 1 that has good insertability and that is minimally invasive can be realized.

As shown in FIG. 1 to FIG. 3, the basket pusher 40 is disposed on the proximal side with respect to the basket 30. When the basket pusher 40 is moved in the longitudinal direction of the outer tube 10, the basket pusher 40 can move the basket 30 in the longitudinal direction of the outer tube 10, thereby releasing the basket 30 from the outer tube 10 or accommodating the basket 30 in the outer tube 10. Although not shown, the basket pusher 40 may include a handle for controlling the position in the longitudinal direction or rotation thereof, on the proximal side with respect to the proximal end 10p of the outer tube 10.

The material forming the basket pusher 40 is preferably a metal, and examples thereof include metals such as stainless steel, carbon steel, and nickel-titanium alloys. Among them, the material forming the basket pusher 40 is preferably stainless steel. When the material forming the basket pusher 40 is stainless steel, the rigidity of the basket pusher 40 can be enhanced. As a result, the force applied to the basket pusher 40 can be efficiently transmitted to the basket 30, and thus, it becomes easier to perform the operation of releasing the basket 30 from the outer tube 10.

As shown in FIG. 1 to FIG. 3 and FIG. 6, the basket 30 includes the first bundling portion 51 at which the plurality of wires 20 are bundled and fixed at the distal portion of the basket 30, and the second bundling portion 52 at which the plurality of wires 20 are bundled and fixed at the proximal portion of the basket 30. As shown in FIG. 6, the basket 30 is formed, between the first bundling portion 51 and the second bundling portion 52, in a cage shape composed of a plurality of bent wires 20, or a cage shape obtained by braiding right-handed spiral wires 20 and left-handed spiral wires 20, for example. Among them, the basket 30 is preferably formed by braiding right-handed spiral wires 20 and left-handed spiral wires 20. When right-handed spiral wires 20 and left-handed spiral wires 20 are braided to form the basket 30, the basket 30 can have a cage shape having a mesh-like wall surface. As a result, an object contained inside the basket 30 is less likely to get out of the basket 30, whereby removal of an abnormal object and promotion of thrombosis are easily and efficiently performed.

Examples of a method for bundling and fixing the plurality of wires 20 at the first bundling portion 51 and the second bundling portion 52 include welding the plurality of wires 20, crimping the plurality of wires 20 together using a separate member, adhering the plurality of wires 20 using an adhesive, and fixing the plurality of wires 20 with a brazing material, and a combination thereof. Among them, crimping and fixing the plurality of wires 20 by the separate member at the first bundling portion 51 and the second bundling portion 52 is preferable. When the plurality of wires 20 are crimped and fixed by the separate member at the first bundling portion 51 and the second bundling portion 52, the plurality of wires 20 are easily and firmly fixed at the first bundling portion 51 and the second bundling portion 52, and the basket 30 is less likely to be broken.

Examples of the separate member that bundles and fixes the plurality of wires 20 at the first bundling portion 51 and the second bundling portion 52 include a ring-shaped member, a member having a C-shaped cross-section obtained by making a cut in a ring, a coil-shaped member obtained by winding a wire material, and a member that binds and fixes the plurality of wires 20 with a string-like object. Among them, the separate member that bundles and fixes the plurality of wires 20 is preferably a ring-shaped member, and more preferably a ring-shaped swaged member. When the separate member that bundles and fixes the plurality of wires 20 is a ring-shaped swaged member, the plurality of wires 20 can be firmly fixed, and the plurality of wires 20 can be less likely to be de-bundled.

As the material forming the separate member that bundles and fixes the plurality of wires 20, the same materials as those for the wires 20 of the basket 30 and the basket pusher 40 can be used, for example. Among them, the material forming the separate member that bundles and fixes the plurality of wires 20 is preferably stainless steel. When the material forming the separate member that bundles and fixes the plurality of wires 20 is stainless steel, the fixing strength of the plurality of wires 20 can be enhanced, and the durability of the separate member that bundles and fixes the plurality of wires 20 can be improved. Further, the material forming the separate member that bundles and fixes the plurality of wires 20 is more preferably a radiopaque material. Examples of the radiopaque material include platinum, gold, tungsten, iridium, palladium, tantalum, and an alloy in which at least one of these is combined. When the material forming the separate member that bundles and fixes the plurality of wires 20 is the radiopaque material, the positions of the first bundling portion 51 and the second bundling portion 52 can be confirmed under X-ray fluoroscopy. Thus, it is possible to grasp the position of the basket 30 in a body.

As shown in FIG. 2, in the state where the basket 30 is accommodated in the outer tube 10, the first bundling portion 51 has the first end 61 being an end portion on the far side with respect to the second bundling portion 52 and the second end 62 being an end portion on the near side with respect to the second bundling portion 52. In other words, the first end 61 is the distal end of the first bundling portion 51 in the state where the basket 30 is accommodated in the outer tube 10, and the second end 62 is the proximal end of the first bundling portion 51 in the state where the basket 30 is accommodated in the outer tube 10.

Preferably, in the state where the basket 30 is accommodated in the outer tube 10, the wires 20 are present on the proximal side with respect to the second end 62 and the wires 20 are not present on the distal side with respect to the first end 61. In the state where the basket 30 is accommodated in the outer tube 10, when the wires 20 are not present on the distal side with respect to the first end 61, the wires 20 are not present at a distal end 30d of the basket 30. As a result, when the distal end 30d of the basket 30 comes into contact with another object such as a tube wall of an in-vivo lumen, the other object can be prevented from being damaged by the wires 20, and the medical device 1 that is minimally invasive can be realized. In addition, in the state where the basket 30 is accommodated in the outer tube 10, when the wires 20 are present on the proximal side with respect to the second end 62, the wires 20 of the basket 30 can be sufficiently bundled and fixed at the first bundling portion 51, and thus, the fixing strength of the wires 20 can be enhanced. In addition, preferably, rounding of the corner portion of the first end 61, i.e., so-called R-processing, has been performed on the first end 61. When the R-processing has been performed on the corner portion of the first end 61, even if the first end 61 comes into contact with another object such as a tube wall of an in-vivo lumen, the other object can be less likely to be damaged by the first end 61.

In at least a partial section of the basket 30, as the basket 30 comes out of the outer tube 10, the angle θ1 on the proximal side between the extending direction L1 of the leading end portion of the outer tube 10 and the straight line L2 passing through the first end 61 and the second end 62 becomes smaller. That is, in at least a partial section of the basket 30, the longer the length by which the basket 30 is outside the outer tube 10 is, the smaller the angle θ1 on the proximal side between the extending direction L1 of the leading end portion of the outer tube 10 and the straight line L2 passing through the first end 61 and the second end 62 becomes. Since, as the basket 30 comes out of the outer tube 10, the angle θ1 on the proximal side between the extending direction L1 of the leading end portion of the outer tube 10 and the straight line L2 passing through the first end 61 and the second end 62 becomes smaller, the distal end portion of the basket 30 bends in accordance with the length by which the basket 30 has come out of the outer tube 10. Accordingly, the basket 30 can be easily pushed to the distal side, and at the same time, the distal end portion of the basket 30 can be less likely to come into contact with the tube wall or the like of the in-vivo lumen. The extending direction L1 of the leading end portion of the outer tube 10 can also be said to be the direction in which the distal end of the outer tube 10 is oriented.

The length of the section in which, as the basket 30 comes out of the outer tube 10, the angle θ1 on the proximal side between the extending direction L1 of the leading end portion of the outer tube 10 and the straight line L2 passing through the first end 61 and the second end 62 becomes smaller is preferably 10% or more, more preferably 15% or more, and further preferably 20% or more of the entire length of the basket 30. When the lower limit value of the proportion of the length of the section of the basket 30 in which the angle θ1 becomes smaller is set to be in the above range, the angle θ1 can be gradually changed in at least a partial section of the basket 30, and the distal end portion of the basket 30 can be less likely to sharply bend to come into contact with the tube wall or the like of the in-vivo lumen. The upper limit value of the proportion of the length of the section of the basket 30 in which the angle θ1 becomes smaller is not limited in particular, and for example, can be set to be 99% or less, 98% or less, or 97% or less of the entire length of the basket 30.

As shown in FIG. 3, preferably, in the state where the predetermined length of the basket 30 has come out of the outer tube 10, the second end 62 is positioned on the distal side with respect to the first end 61. In the state where the predetermined length of the basket 30 has come out of the outer tube 10, when the second end 62 is positioned on the distal side with respect to the first end 61, the distal end portion of the basket 30 is in a state of being bent toward the proximal side. As a result, when the basket 30 is pushed to the distal side in order to release the basket 30 from the outer tube 10 to the outside, the distal end 30*d* of the basket 30 is less likely to come into contact with the tube wall or the like of the in-vivo lumen, and thus, the medical device 1 that is further minimally invasive can be realized.

As shown in FIG. 3, preferably, when the predetermined length of the basket 30 has come out of the outer tube 10, the angle θ1 on the proximal side between the extending direction L1 of the leading end portion of the outer tube 10 and the straight line L2 passing through the first end 61 and the second end 62 becomes 0 degrees or more and 90 degrees or less (including 0 degrees), and the predetermined length is a length of ⅟10 or more and ¾ or less of the length from a proximal end 30*p* of the basket 30 to the distal end 30*d* of the basket 30. That is, preferably, in a process where the basket 30 is released from the outer tube 10, when the basket 30 has been released from the outer tube 10 to the outside by a length of ⅟10 or more and ¾ or less of the entire length of the basket 30, the angle θ1 on the proximal side between the extending direction L1 of the leading end portion of the outer tube 10 and the straight line L2 passing through the first end 61 and the second end 62 becomes 0 degrees or more and 90 degrees or less (including 0 degrees). The entire length of the basket 30 refers to the length from the proximal end 30*p* of the basket 30 to the distal end 30*d* of the basket 30 in a state where the entirety of the basket 30 has come out of the outer tube 10. That is, preferably, the predetermined length is a length of ⅟10 or more and ¾ or less of the length from the proximal end 30*p* of the basket 30 to the distal end 30*d* of the basket 30 in the state where the entirety of the basket 30 has come out of the outer tube 10.

When the basket 30 has come out of the outer tube 10 by the length of ⅟10 or more and ¾ or less of the length from the proximal end 30*p* of the basket 30 to the distal end 30*d* of the basket 30, the angle θ1 on the proximal side between the extending direction L1 of the leading end portion of the outer tube 10 and the straight line L2 passing through the first end 61 and the second end 62 becomes 0 degrees or more and 90 degrees or less (including 0 degrees). Therefore, in the process of releasing the basket 30 from the outer tube 10, the distal end portion of the basket 30 enters a state of being bent so as to be oriented toward the proximal side. Therefore, when the basket 30 has been pushed toward the distal side in order to release the basket 30 from the outer tube 10, the distal end portion of the basket 30 is less likely to come into contact with the tube wall or the like of the in-vivo lumen, and thus, can be less likely to damage the tube wall. Accordingly, the medical device 1 that is minimally invasive can be realized.

In a state where the predetermined length of the basket 30 has come out of the outer tube 10, the angle θ1 on the proximal side between the extending direction L1 of the leading end portion of the outer tube 10 and the straight line L2 passing through the first end 61 and the second end 62 is preferably 90 degrees or less, more preferably 85 degrees or less, further preferably 80 degrees or less, and still further preferably 75 degrees or less. When the upper limit value of the angle θ1 on the proximal side between the extending direction L1 of the leading end portion of the outer tube 10 and the straight line L2 passing through the first end 61 and the second end 62 is set to be in the above range, the effect that the distal end portion of the basket 30 is less likely to come into contact with the tube wall of the in-vivo lumen can be enhanced, and the minimal invasiveness of the medical device 1 can be further improved.

As shown in FIG. 3, preferably, in the state where the predetermined length of the basket 30 has come out of the outer tube 10, the first bundling portion 51 is positioned on the proximal side with respect to the distal end 30*d* of the basket 30. When the first bundling portion 51 where the rigidity tends to be higher than the other part of the basket 30 is positioned on the proximal side with respect to the distal end 30*d* of the basket 30, the distal end portion of the basket 30 becomes flexible. As a result, when the basket 30 is transported to a target site or indwelled at the target site, even if the distal end portion of the basket 30 comes into contact with the tube wall or the like of the in-vivo lumen, the distal end portion of the basket 30 is less likely to damage the tube wall or the like, and thus, the safety of the medical device 1 can be enhanced.

It is sufficient that the predetermined length of the basket 30 is ⅟10 or more of the length from the proximal end 30*p* of the basket 30 to the distal end 30*d* of the basket 30 in the state where the entirety of the basket 30 has come out of the outer tube 10, but the predetermined length of the basket 30 is preferably ⅛ or more, more preferably ⅙ or more, and further preferably ⅕ or more. When the lower limit value of the predetermined length of the basket 30 is set to be in the above range, the radius of the bending of the distal end portion of the basket 30 becomes large, and even if the distal end portion of the basket 30 comes into contact with the tube wall or the like of the in-vivo lumen, the distal end portion of the basket 30 is less likely to damage the tube wall. It is sufficient that the predetermined length of the basket 30 is a length of ¾ or less of the length from the proximal end 30$p$ of the basket 30 to the distal end 30$d$ of the basket 30 in the state where the entirety of the basket 30 has come out of the outer tube 10, but the predetermined length of the basket 30 is preferably ⅚ or less, more preferably ⁷⁄₁₀ or less, and further preferably ⅔ or less. When the upper limit value of the predetermined length of the basket 30 is set to be in the above range, the distal end portion of the basket 30 bends immediately after the distal end 30$d$ of the basket 30 has come out of the outer tube 10, and thus, the distal end 30$d$ of the basket 30 can be less likely to come into contact with the tube wall of the in-vivo lumen.

FIG. 4 is a cross-sectional view, parallel to the longitudinal direction of the outer tube 10, of the distal end portion of the medical device 1 in a state where the entirety of the basket 30 has come out of the outer tube 10 and no external force is applied to the basket 30. In FIG. 4, only some wires 20 out of the plurality of wires 20 of the basket 30 are shown, and the other wires 20 are not shown. In FIG. 4, the right side of the drawing is the proximal side and the left side of the drawing is the distal side.

As shown in FIG. 4, preferably, in the state where the entirety of the basket 30 has come out of the outer tube 10 and no external force is applied to the basket 30, the angle θ1 on the proximal side between the extending direction L1 of the leading end portion of the outer tube 10 and the straight line L2 passing through the first end 61 and the second end 62 is more than 90 degrees and 180 degrees or less (including 180 degrees). FIG. 4 shows a configuration in which the angle θ1 on the proximal side between the extending direction L1 of the leading end portion of the outer tube 10 and the straight line L2 passing through the first end 61 and the second end 62 is 180 degrees. In the state where the entirety of the basket 30 has come out of the outer tube 10 and no external force is applied to the basket 30, when the angle θ1 is more than 90 degrees and 180 degrees or less (including 180 degrees), the degree of the bending of the distal end portion of the basket 30 can be made smaller than that in the state where the predetermined length of the basket 30 has come out of the outer tube 10 after the basket 30 accommodated in the outer tube 10 has begun to come out of the outer tube 10. That is, in the state where the entirety of the basket 30 has come out of the outer tube 10 and no external force is applied to the basket 30, a state where the distal end portion of the basket 30 is not bent toward the proximal side and is oriented toward the distal side is easily established. As a result, the basket 30 is easily expanded and disposed at the target site.

In the state where the entirety of the basket 30 has come out of the outer tube 10 and no external force is applied to the basket 30, the angle θ1 on the proximal side between the extending direction L1 of the leading end portion of the outer tube 10 and the straight line L2 passing through the first end 61 and the second end 62 is preferably more than 90 degrees, more preferably 120 degrees or more, and further preferably 135 degrees or more. When the lower limit value of the angle θ1 in the state where the entirety of the basket 30 has come out of the outer tube 10 and no external force is applied to the basket 30 is set to be in the above range, the distal end portion of the basket 30 can be easily oriented toward the distal side and the expanded basket 30 can be easily disposed at the target site.

As shown in FIG. 4, preferably, in the state where the entirety of the basket 30 has come out of the outer tube 10 and no external force is applied to the basket 30, the second end 62 is positioned on the distal side with respect to the first end 61. In the state where the entirety of the basket 30 has come out of the outer tube 10 and no external force is applied to the basket 30, when the second end 62 is positioned on the distal side with respect to the first end 61, the distal end portion of the basket 30 in an expanded state enters a state of being bent toward the proximal side. As a result, the first bundling portion 51 of the basket 30 is less likely to come into contact with the tube wall of the in-vivo lumen, and thus, the tube wall can be less likely to be damaged by the first bundling portion 51. Accordingly, the medical device 1 that is minimally invasive can be realized.

Preferably, as shown in FIG. 2, in the state where the basket 30 is accommodated in the outer tube 10, the first bundling portion 51 is positioned on the distal side with respect to a distal end 20$d$ of the wires 20. The first bundling portion 51 is the part at which the plurality of wires 20 of the basket 30 are bundled and fixed, and thus, the rigidity tends to be higher than the other part of the basket 30. In the state where the basket 30 is accommodated in the outer tube 10, when the first bundling portion 51 is positioned on the distal side with respect to the distal end 20$d$ of the wires 20, the rigidity of the distal end portion of the basket 30 is enhanced. As a result, the force applied from the hand side to push the basket 30 to the distal side can be efficiently transmitted to the basket 30, and thus, the basket 30 can be easily released from the outer tube 10.

Preferably, as shown in FIG. 3 and FIG. 4, in the state where the predetermined length of the basket 30 has come out of the outer tube 10, the first bundling portion 51 is positioned outside the basket 30, and in the state where the entirety of the basket 30 has come out of the outer tube 10 and no external force is applied to the basket 30, the first bundling portion 51 is positioned inside the basket 30. That is, preferably, in the state where the basket 30 has come out of the outer tube 10 by the predetermined length and the entirety of the basket 30 has not come out of the outer tube 10, the first bundling portion 51 is positioned outside the basket 30, and in the state where the entirety of the basket 30 has come out of the outer tube 10 and no external force is applied to the basket 30, the first bundling portion 51 is positioned inside the basket 30. When the first bundling portion 51 at which the plurality of wires 20 of the basket 30 are bundled and fixed and the rigidity easily becomes higher than the other part of the basket 30 is positioned outside the basket 30 in the state where the predetermined length of the basket 30 has come out of the outer tube 10, the force to push the basket 30 to the distal side is easily transmitted to the first bundling portion 51 at the distal end portion of the basket 30. Therefore, the basket 30 can be easily released from the outer tube 10 to the outside. When the first bundling portion 51 is positioned inside the basket 30 in the state where the entirety of the basket 30 has come out of the outer tube 10 and no external force is applied to the basket 30, the first bundling portion 51 is not positioned at the distal end 30$d$ of the basket 30 and thus, the distal end portion of the basket 30 becomes flexible. Therefore, even if the distal end portion of the basket 30 released from the outer tube 10 comes into contact with the tube wall or the like of the in-vivo lumen, the basket 30 is less likely to damage the tube wall or the like, and thus minimal invasiveness of the medical device 1 can be improved.

Preferably, the plurality of wires 20 of the basket 30 include a first wire group 21 and a second wire group 22, and the length of the wire 20 of the first wire group 21 is shorter than the length of the wire 20 of the second wire group 22. The length of each wire 20 is the length from the distal end 20*d* to a proximal end 20*p* of a single wire 20. When the length of the wire 20 of the first wire group 21 is shorter than the length of the wire 20 of the second wire group 22, if the state where the entirety of the basket 30 has come out of the outer tube 10 and no external force is applied to the basket 30 is established, the part where the first wire group 21 of the basket 30 is present is easily positioned inside the bending of the basket 30. Therefore, when the entirety of the basket 30 is exposed from the outer tube 10 to allow the distal end portion of the basket 30 to bend toward the proximal side, the start point or the position of the bending is easily controlled. As a result, the effect of causing the distal end portion of the basket 30 to be less likely to come into contact with another object can be further enhanced. The number of the wires 20 of the first wire group 21 may be one or may be plural. The number of the wires 20 of the second wire group 22 may be one or may be plural as well.

The length of the wire 20 of the first wire group 21 is preferably less than 100%, more preferably 99.5% or less, and further preferably 99% or less of the length of the wire 20 of the second wire group 22. When the upper limit value of the ratio between the length of the wire 20 of the first wire group 21 and the length of the wire 20 of the second wire group 22 is set to be in the above range, if the state where the entirety of the basket 30 has come out of the outer tube 10 and no external force is applied to the basket 30 is established, the first wire group 21 is easily positioned inside the bending of the basket 30, and thus, the bending of the basket 30 is easily controlled. The lower limit value of the ratio between the length of the wire 20 of the first wire group 21 and the length of the wire 20 of the second wire group 22 is not limited in particular, and can be 90% or more, 93% or more, or 95% or more, for example.

FIG. 5 is a cross-sectional view, perpendicular to the longitudinal direction of the basket pusher 40, of the basket 30 of the medical device 1. Preferably, as shown in FIG. 5, the plurality of wires 20 of the basket 30 further include a third wire group 23, the length of the wire 20 of the third wire group 23 is longer than the length of the wire 20 of the first wire group 21, and shorter than the length of the wire 20 of the second wire group 22, and, in a cross-section perpendicular to the extending direction of the basket pusher 40, a distance D2 between the first wire group 21 and the second wire group 22 is longer than a distance D3 between the first wire group 21 and the third wire group 23. That the length of the wire 20 of the third wire group 23 is longer than the length of the wire 20 of the first wire group 21 and is shorter than the length of the wire 20 of the second wire group 22 means that, among the first wire group 21, the second wire group 22, and the third wire group 23, the length of the wire 20 of the first wire group 21 is the shortest and the length of the wire 20 of the second wire group 22 is the longest. When the distance D2 between the first wire group 21 and the second wire group 22 is longer than the distance D3 between the first wire group 21 and the third wire group 23, among the first wire group 21, the second wire group 22, and the third wire group 23, the distance between the first wire group 21 in which the length of the wire 20 is the shortest and the second wire group 22 in which the length of the wire 20 is the longest can be made large. As a result, when the basket 30 has come out of the outer tube 10 and the distal end portion of the basket 30 bends, the first wire group 21 in which the length of the wire 20 is the shortest and that has a large distance from the second wire group 22 in which the length of the wire 20 is the longest easily serves as the start point of the bending, and thus, the bending of the basket 30 is easily controlled. The number of the wires 20 of the third wire group 23 may be one or may be plural as well.

In a cross-section perpendicular to the extending direction of the basket pusher 40, the distance D2 between the first wire group 21 and the second wire group 22 is preferably 1.1 times or more, more preferably 1.2 times or more, and further preferably 1.3 times or more the distance D3 between the first wire group 21 and the third wire group 23. When the lower limit value of the ratio between the distance D2 between the first wire group 21 and the second wire group 22 and the distance D3 between the first wire group 21 and the third wire group 23 is set to be in the above range, the distance D2 between the first wire group 21 and the second wire group 22 can be made sufficiently large as compared with the distance D3 between the first wire group 21 and the third wire group 23. Accordingly, in the basket 30, the first wire group 21 easily serves as the start point of the bending. In a cross-section perpendicular to the extending direction of the basket pusher 40, the distance D2 between the first wire group 21 and the second wire group 22 is preferably 5 times or less, more preferably 4 times or less, and further preferably 3 times or less the distance D3 between the first wire group 21 and the third wire group 23. When the upper limit value of the ratio between the distance D2 between the first wire group 21 and the second wire group 22 and the distance D3 between the first wire group 21 the third wire group 23 is set to be in the above range, the basket 30 is less likely to be excessively large. As a result, the outer diameter of the outer tube 10 can also be prevented from becoming excessively large.

The plurality of wires 20 of the basket 30 may further include a wire group different from the first wire group 21, the second wire group 22, and the third wire group 23. The wire group different from the first wire group 21, the second wire group 22, and the third wire group 23 refers to a wire group in which at least one of the length, rigidity, outer diameter, forming material, and the like is different from those of the wires 20 of the first wire group 21, the second wire group 22, and the third wire group 23. The number of wires of the wire group different from the first wire group 21, the second wire group 22, and the third wire group 23 may be one or may be plural as well.

As shown in FIG. 2 and FIG. 4, preferably, in the state where the basket 30 is accommodated in the outer tube 10, the second bundling portion 52 has one end 71 being an end portion on the near side with respect to the first bundling portion 51 and the other end 72 being an end portion on the far side with respect to the first bundling portion 51, and in the state where the entirety of the basket 30 has come out of the outer tube 10 and no external force is applied to the basket 30, the one end 71 is positioned on the distal side with respect to the other end 72. That is, preferably, between when the basket 30 is accommodated in the outer tube 10 and when the entirety of the basket 30 has come out of the outer tube 10 and no external force is applied to the basket 30, the positional relationship in the distal-proximal direction between the first end 61 and the second end 62 of the first bundling portion 51 is interchanged, but the positional relationship in the distal-proximal direction between the one end 71 and the other end 72 of the second bundling portion

52 is not interchanged. That is, preferably, between the state where the basket 30 is accommodated in the outer tube 10 and the state where the entirety of the basket 30 has come out of the outer tube 10 and no external force is applied to the basket 30, the positional relationship in the distal-proximal direction between the first end 61 and the second end 62 of the first bundling portion 51 is inverted, but the positional relationship in the distal-proximal direction between the one end 71 and the other end 72 of the second bundling portion 52 is not inverted. In the state where the entirety of the basket 30 has come out of the outer tube 10 and no external force is applied to the basket 30, when the one end 71 is positioned on the distal side with respect to the other end 72, the positional relationship in the distal-proximal direction between the one end 71 and the other end 72 of the second bundling portion 52 is not interchanged between when the basket 30 is accommodated in the outer tube 10 and when the entirety of the basket 30 has come out of the outer tube 10 and no external force is applied to the basket 30. Therefore, the basket 30 released from the outer tube 10 is easily withdrawn into the outer tube 10 again, and thus, the medical device 1 that has good operability can be realized. Since the configuration of the second bundling portion 52 of the basket 30 can be made simple, the production efficiency of the medical device 1 can be enhanced.

As shown in FIG. 2 to FIG. 4, the second bundling portion 52 is preferably positioned on the proximal side with respect to the proximal end 20p of each wire 20. Similar to the first bundling portion 51, the second bundling portion 52 is the part at which the plurality of wires 20 of the basket 30 are bundled and fixed, and thus, the rigidity tends to be higher than the other part of the basket 30. When the second bundling portion 52 is positioned on the proximal side with respect to the proximal end 20p of each wire 20, the rigidity of the proximal end portion of the basket 30 can be enhanced, and the force applied from the hand side to push the basket 30 to the distal side can be efficiently transmitted to the basket 30. As a result, the medical device 1 in which the basket 30 is easily released from the outer tube 10 can be realized.

As shown in FIG. 2 to FIG. 4, preferably, the wires 20 are present on the distal side with respect to the one end 71 and the wires 20 are not present on the proximal side with respect to the other end 72. When the wires 20 are present on the distal side with respect to the one end 71 and the wires 20 are not present on the proximal side with respect to the other end 72, no wire 20 is present at a proximal end 30p of the basket 30. Therefore, when the basket 30 released from the outer tube 10 is pulled back into the outer tube 10, the wires 20 are less likely to come into contact with the outer tube 10, and the basket 30 is easily and smoothly withdrawn into the outer tube 10.

As shown in FIG. 1 to FIG. 4, preferably, a connection member 80 is provided on the proximal side with respect to the basket 30 and on the distal side with respect to the basket pusher 40. The connection member 80 is a member that connects the basket 30 and the basket pusher 40 to each other. When the connection member 80 is provided on the proximal side with respect to the basket 30 and on the distal side with respect to the basket pusher 40, connection between the basket 30 and the basket pusher 40 can be easily performed.

Preferably, the connection member 80 is severable. That is, preferably, the basket 30 can be detached from the basket pusher 40 by severing the connection member 80. In the case where the connection member 80 is severable, if the connection member 80 is severed after the basket 30 has been transported to a target site, the basket 30 is detached from the basket pusher 40, and thus, the basket 30 is easily indwelled in the target site.

As a method for severing the connection member 80, various methods such as a mechanical severing mechanism, fusion cutting, thermal, electrical, and chemical severing can used. Examples of the connection member 80 include rod-like objects, string-like objects, clips, members fitted to each other such as recesses and projections, etc. As the material forming the connection member 80, synthetic resins, metals, etc., can be used. The connection member 80 may be a member different from the basket 30 or the basket pusher 40, or may be a part of the basket 30 or the basket pusher 40.

Preferably, the material forming the connection member 80 has a property of melting due to heat, and the medical device 1 has a heating mechanism 90 for heating the connection member 80. When the material forming the connection member 80 has a property of melting due to heat and the medical device 1 has the heating mechanism 90, the connection member 80 can be melted and broken by the heating mechanism 90 heating the connection member 80, whereby the basket 30 can be detached from the basket pusher 40. Therefore, the basket 30 and the basket pusher 40 can be firmly connected by the connection member 80 until the heating mechanism 90 is activated, and the connection member 80 can be easily severed when the heating mechanism 90 is activated. Thus, the basket 30 can be easily and reliably indwelled.

As the material forming the connection member 80 and having a property of melting due to heat, thermoplastic resins are preferable, and among them, PVA (polyvinyl alcohol) is more preferable. When the material forming the connection member 80 is PVA, the connection member 80 can be more easily severed, and thus, the medical device 1 that is easily handled can be realized.

Preferably, the heating mechanism 90 is connected to the basket pusher 40. When the heating mechanism 90 is connected to the basket pusher 40, the connection member 80 can be heated via the basket pusher 40, and thus, it is not necessary to additionally provide a member for transmitting the heat of the heating mechanism 90 to the connection member 80. Accordingly, the size of the medical device 1 can be reduced.

Preferably, the first bundling portion 51 and the second bundling portion 52 include a radiopaque material. When the first bundling portion 51 and the second bundling portion 52 include the radiopaque material, the positions of the first bundling portion 51 and the second bundling portion 52 can be confirmed under X-ray fluoroscopy. As a result, the position of the basket 30 in a body can be grasped.

Examples of the radiopaque material include platinum, gold, tungsten, iridium, palladium, tantalum, and an alloy in which at least one of these is combined.

Each wire 20 of the basket 30 preferably includes a superelastic alloy. When each wire 20 includes a superelastic alloy, the basket 30 becomes excellent in elasticity. When the basket 30 is excellent in elasticity, the deformation amount of the basket 30 can be made large. Therefore, the basket 30 can be accommodated in the outer tube 10 having a small outer diameter, and the basket 30 can be expanded to a large extent when the basket 30 comes out of the outer tube 10.

Preferably, each wire 20 of the basket 30 includes the radiopaque material. When each wire 20 includes the radiopaque material, the position and the state of the expansion of the basket 30 can be confirmed under X-ray fluoroscopy, and the procedure is easily and smoothly performed.

As described above, the medical device of the present invention includes: an outer tube having a distal end and a proximal end; a basket disposed in an inner cavity of the outer tube and having a plurality of wires, the basket being expandable when having come out of the outer tube; and a basket pusher disposed on a proximal side with respect to the basket. The basket includes a first bundling portion at which the plurality of wires are bundled and fixed at a distal portion of the basket, and a second bundling portion at which the plurality of wires are bundled and fixed at a proximal portion of the basket. In a state where the basket is accommodated in the outer tube, the first bundling portion has a first end being an end portion on a far side with respect to the second bundling portion and a second end being an end portion on a near side with respect to the second bundling portion. In at least a partial section of the basket, as the basket comes out of the outer tube, an angle between an extending direction of a leading end portion of the outer tube and a straight line passing through the first end and the second end becomes smaller. Since the medical device of the present invention has such a configuration, in a process where the basket accommodated in the outer tube comes out of the outer tube, the distal end portion of the basket enters a state of being bent. Therefore, when the basket is released from the outer tube, the distal end portion of the basket is less likely to come into contact with the tube wall of the in-vivo lumen, and thus, can be less likely to damage the tube wall. Accordingly, a medical device that is minimally invasive can be realized.

This application claims priority to Japanese Patent Application No. 2022-034902, filed on Mar. 8, 2022. All of the contents of the Japanese Patent Application No. 2022-034902, filed on Mar. 8, 2022, are incorporated by reference herein.

REFERENCE SIGNS LIST

1: medical device
10: outer tube
10*d*: distal end of the outer tube
10*p*: proximal end of the outer tube
20: wire
20*d*: distal end of the wire
20*p*: proximal end of the wire
21: first wire group
22: second wire group
23: third wire group
30: basket
30*d*: distal end of the basket
30*p*: proximal end of the basket
40: basket pusher
51: first bundling portion
52: second bundling portion
61: first end of the first bundling portion
62: second end of the first bundling portion
71: one end of the second bundling portion
72: other end of the second bundling portion
80: connection member
90: heating mechanism
L1: extending direction of the leading end portion of the outer tube
L2: straight line passing through the first end and the second end θ1: angle on the proximal side between the extending direction of the leading end portion of the outer tube and the straight line passing through the first end and the second end
D2: distance between the first wire group and the second wire group
D3: distance between the first wire group and the third wire group

The invention claimed is:

1. A medical device comprising:
an outer tube having a distal end and a proximal end;
a basket disposed in an inner cavity of the outer tube and having a plurality of wires, the basket being expandable when having come out of the outer tube; and
a basket pusher disposed on a proximal side with respect to the basket, wherein
the basket includes a first bundling portion at which the plurality of wires are bundled and fixed at a distal portion of the basket, and a second bundling portion at which the plurality of wires are bundled and fixed at a proximal portion of the basket,
in a state where the basket is accommodated in the outer tube, the first bundling portion has a first end being an end portion on a far side with respect to the second bundling portion and a second end being an end portion on a near side with respect to the second bundling portion, and
the outer tube and the basket are configured so that in at least a partial section of the basket, as the basket comes out of the outer tube, an angle on the proximal side between an extending direction of a leading end portion of the outer tube and a straight line passing through the first end and the second end of the first bundling portion becomes smaller.

2. The medical device according to claim 1, wherein the basket is configured so that in a state where a predetermined length of the basket has come out of the outer tube, the second end is positioned on a distal side with respect to the first end.

3. The medical device according to claim 1, wherein the outer tube and the basket are configured so that when a predetermined length of the basket has come out of the outer tube, the angle on the proximal side between the extending direction of the leading end portion of the outer tube and the straight line passing through the first end and the second end of the first bundling portion becomes 0 degrees or more and 90 degrees or less (including 0 degrees), and the predetermined length is a length of $\frac{1}{10}$ or more and $\frac{3}{4}$ or less of a length from a proximal end of the basket to a distal end of the basket.

4. The medical device according to claim 1, wherein the outer tube and the basket are configured so that in a state where an entirety of the basket has come out of the outer tube and no external force is applied to the basket, the angle on the proximal side between the extending direction of the outer tube and the straight line passing through the first end and the second end of the first bundling portion is more than 90 degrees and 180 degrees or less (including 180 degrees).

5. The medical device according to claim 1, wherein in a state where an entirety of the basket has come out of the outer tube and no external force is applied to the basket, the second end is positioned on a distal side with respect to the first end.

6. The medical device according to claim 1, wherein the basket is configured so that in a state where a predetermined length of the basket has come out of the outer tube, the first bundling portion is positioned outside the basket, and in a state where an entirety of the basket has come out of the outer tube and no external force is applied to the basket, the first bundling portion is positioned inside the basket.

7. The medical device according to claim 1, wherein the plurality of wires of the basket include a first wire group and a second wire group, and a length of the wire of the first wire group is shorter than a length of the wire of the second wire group.

8. The medical device according to claim 7, wherein the plurality of wires of the basket further include a third wire group, a length of the wire of the third wire group is longer than the length of the wire of the first wire group and shorter than the length of the wire of the second wire group, and in a cross-section perpendicular to an extending direction of the basket pusher, a distance between the first wire group and the second wire group is longer than a distance between the first wire group and the third wire group.

9. The medical device according to claim 1, wherein the basket is configured so that in the state where the basket is accommodated in the outer tube, the second bundling portion has one end being an end portion on a near side with respect to the first bundling portion and another end being an end portion on a far side with respect to the first bundling portion, and in a state where an entirety of the basket has come out of the outer tube and no external force is applied to the basket, the one end is positioned on a distal side with respect to the another end.

10. The medical device according to claim 1, comprising a connection member on the proximal side with respect to the basket and on a distal side with respect to the basket pusher.

11. The medical device according to claim 1, wherein the first bundling portion and the second bundling portion include a radiopaque material.

12. The medical device according to claim 1, wherein each wire of the basket includes a superelastic alloy.

13. The medical device according to claim 1, wherein each wire of the basket includes a radiopaque material.

* * * * *